(12) United States Patent
Al-Ali

(10) Patent No.: US 8,897,847 B2
(45) Date of Patent: Nov. 25, 2014

(54) DIGIT GAUGE FOR NONINVASIVE OPTICAL SENSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 127 days.

(21) Appl. No.: 12/727,097

(22) Filed: Mar. 18, 2010

(65) Prior Publication Data

US 2010/0241033 A1  Sep. 23, 2010

Related U.S. Application Data

(60) Provisional application No. 61/162,669, filed on Mar. 23, 2009.

(51) Int. Cl.
*A61B 5/00* (2006.01)
*A61B 5/1455* (2006.01)
*A61B 5/107* (2006.01)
*A61B 5/024* (2006.01)

(52) U.S. Cl.
CPC ........... *A61B 5/14552* (2013.01); *A61B 5/6838* (2013.01); *A61B 5/02416* (2013.01); *A61B 5/107* (2013.01); *A61B 5/6826* (2013.01); *A61B 5/1075* (2013.01)
USPC ....................................... 600/323

(58) Field of Classification Search
USPC ....................................... 600/587
See application file for complete search history.

(56) References Cited

U.S. PATENT DOCUMENTS

| | | | |
|---|---|---|---|
| 4,631,783 A * | 12/1986 | Hayashi | ................ 24/16 PB |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,086,229 A * | 2/1992 | Rosenthal et al. | ....... 250/339.12 |
| 5,163,438 A | 11/1992 | Gordon et al. | |
| 5,278,627 A | 1/1994 | Aoyagi et al. | |
| 5,337,744 A | 8/1994 | Branigan | |
| 5,341,805 A | 8/1994 | Stavridi et al. | |
| 5,353,513 A * | 10/1994 | Round | ......................... 33/555.2 |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |

(Continued)

FOREIGN PATENT DOCUMENTS

GB     2043438     * 10/1980

*Primary Examiner* — Brian Szmal
*Assistant Examiner* — H. Q. Nguyen
(74) *Attorney, Agent, or Firm* — Knobbe Martens Olson & Bear LLP

(57) ABSTRACT

Embodiments of the present disclosure include a digit gauge used to ensure the size of a patient's digit is appropriate for the medical sensor applied thereto.

17 Claims, 2 Drawing Sheets

(56) References Cited

U.S. PATENT DOCUMENTS

| | | |
|---|---|---|
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |

(56) References Cited

U.S. PATENT DOCUMENTS

| | | |
|---|---|---|
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| 8,141,440 B2 * | 3/2012 | Gammon et al. ........ 73/864.63 |
| 8,145,288 B2 * | 3/2012 | Baker, Jr. ................ 600/344 |
| 2007/0228754 A1 * | 10/2007 | Rankin ..................... 294/137 |
| 2008/0058622 A1 * | 3/2008 | Baker ....................... 600/344 |
| 2009/0043180 A1 * | 2/2009 | Tschautscher et al. .... 600/323 |
| 2009/0062694 A1 * | 3/2009 | MacDonald ............. 600/587 |

* cited by examiner

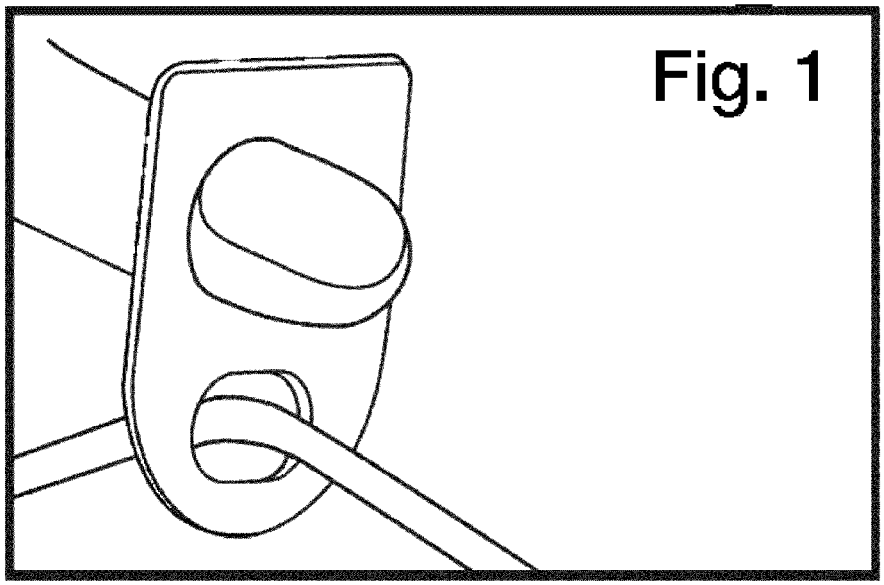
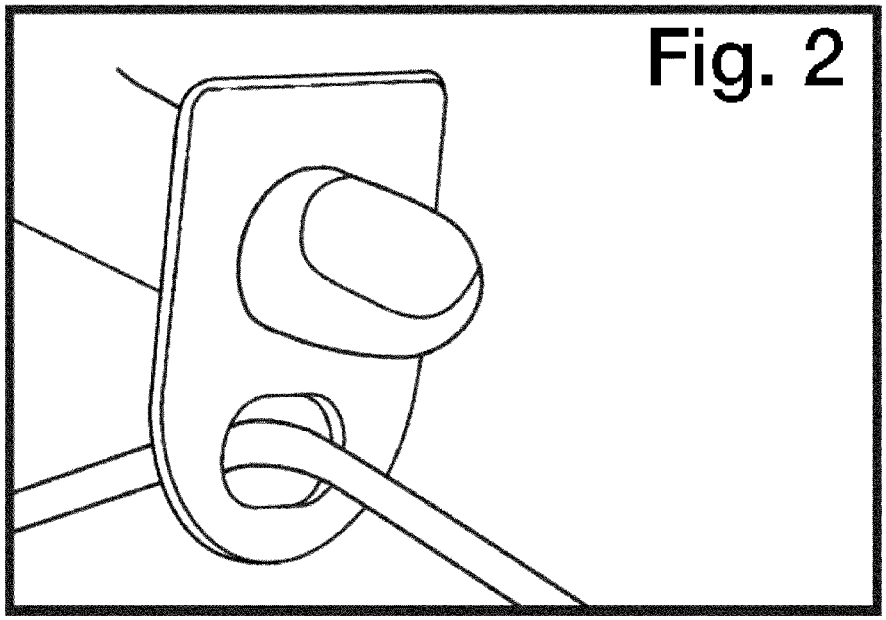

DIGIT GAUGE FOR NONINVASIVE OPTICAL SENSOR

REFERENCE TO RELATED APPLICATIONS

The present application claims priority benefit under 35 U.S.C. §119(e) from U.S. Provisional Application No. 61/162,669, filed Mar. 23, 2009, entitled "Digit Gauge for Noninvasive Optical Sensor," which is incorporated herein by reference.

BACKGROUND OF THE INVENTION

1. Field of the Invention

The present disclosure relates to medical sensors and specifically to noninvasive optical sensors that include light sources and light detectors configured to output signals responsive to an attenuation of light by body tissue such that the output signals are indicative of one or more physiological parameters of the tissue.

2. Description of the Related Art

Pulse oximetry has become a standard of care in many patient monitoring environments. In general, an oximeter system is capable of determining often a variety of measurement values for various blood parameters including oxygenated hemoglobin, carboxyhemoglobin, methemoglobin, total hemoglobin, fractional saturation, and the like. Additionally, today's commercially available oximeters from, for example, Masimo Corporation of Irvine Calif., may advantageously measure other physiological parameters including pulse rate, indications of perfusion, sleep apnea, indications of drug use, possible heart diagnoses, ventilation, hydration and the like.

Oximeter systems generally include one or more noninvasive optical sensors applied to a digit of a patient. The sensors also communicate, often through a cable, with an instrument configured to manage sensor activation and receive sensor output signals. The instrument processes the output signals to determine output values for some or all of the foregoing patient measurements. The noninvasive sensors may be reusable, disposable, or hybrids having reusable and disposable portions. The sensors are usually designed for a particular cross-sectional sized digit, and are often available in sizes including adult, slender digit, pediatric, neonatal and the like.

SUMMARY OF INVENTION

Often, the instrument communicating with a particular sensor includes in its processing some assumptions about the sensor, or at least the tissue associated with the sensor. For example, in some instruments, the processing includes application of a calibration curve to determine output values for a given measurement. The calibration curve generally includes one or more often complicated relationships between processed signals responsive to output voltages of the sensor and clinical data of monitored patients. These relationships are often dependent upon whether the tissue being measured belongs to an adult digit, a pediatric digit, a neonatal digit or the like.

However, in the case of at least reusable optical sensors, care givers may not be sure which type of sensor is appropriate for the cross-sectional size of the particular digit of their patient. The inappropriate choice of sensor may be in part due to readily proximate supplies, misunderstandings by staff, the inherent disorder of an emergency situation, misguided cost cutting measures, or the like.

Based on at least the foregoing, there is a need for a straightforward, relatively quick match between a size of a measurement site and an optical sensor. Accordingly, embodiments of the present disclosure include a digit gauge configured for straightforward relatively quick use. In additional embodiments, the digit gauge is fixedly associated with a particular sensor to provide for consistent size matching between digits and sensors without a risk of loss of the sizing device.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The following drawings and the associated descriptions are provided to illustrate embodiments of the present disclosure and do not limit the scope of the claims.

FIG. 1 shows a perspective simplified illustration of an exemplary embodiment of a digit gauge where a digit size matches an associated sensor.

FIG. 2 shows a perspective simplified illustration of an exemplary embodiment of the digit gauge of FIG. 1, where a digit size does not match an associated sensor.

DETAILED DESCRIPTION OF THE PREFERRED EMBODIMENT

Figure 3:
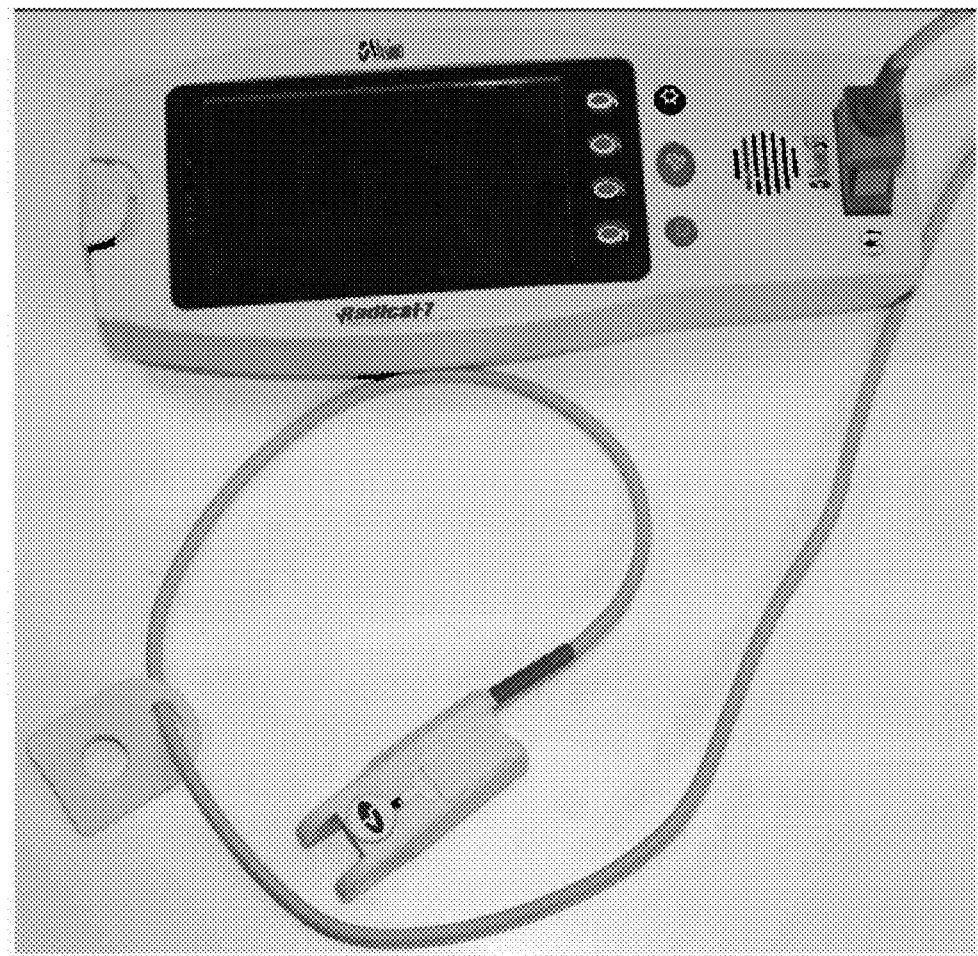
FIG. 3 shows a perspective view of a patient monitoring system including a monitoring instrument, an optical sensor, a connecting cable, and an exemplary digit gauge fixedly associated with the connecting cable and optical sensor.

Embodiments of the present disclosure include a digit gauge associated with an optical sensor of a patient monitoring system. In an embodiment, the monitoring instrument is configured to accept different sensors where some sensors are specifically designed for different cross-sectional sizes of patient tissue. For example, sensor often are available in adult, slender adult, pediatric, neonatal and the like. In some cases, the instrument may provide less accurate measurements when an attached sensor is placed on a mismatched patient's digit. Accordingly, embodiments of the digit gauge advantageously provide a quick, straightforward measurement to determine whether the sensor matches the patient's digit size. In an embodiment, an opening is sized to accept a patient's digit to indicate whether the digit matches the associated sensor. For example, in an embodiment, the digit gauge includes a tab with a substantially circular or circular opening. In various embodiments, how the digit fits through the opening dictates whether the sensor is appropriately sized. In some embodiments, the tab is affixed to a portion of the sensor and/or cable to conveniently provide consistent measurements for a particular sensor and to avoid misplacement of the tab.

To facilitate a complete understanding of the invention, the remainder of the detailed description describes the invention with reference to the drawings, wherein like reference numbers are referenced with like numerals throughout.

FIGS. 1-2 illustrate the digit gauge including a plastic tab having a measurement portion and a sensor association portion. In an embodiment, the measurement portion includes a circular or substantially circular or oval opening capable of accepting a digit of a potential patient to be monitored. The gauge is slid over, preferably the ring finger of the non-dominate hand. When the gauge stops sliding on the finger because the finger becomes too large to further slide through the opening, the caregiver inspects the gauge to see whether a cuticle of the finger is visible through the gauge. When it is not (FIG. 1), the finger size is appropriately matched to the associated sensor. When the finger cuticle can be seen (FIG. 2), in that the gauge slid beyond the cuticle, the caregiver should select another digit for testing with the gauge or use a different sized sensor.

The digit gauge of FIGS. 1-2 also includes the sensor association portion. As shown, the association portion includes an opening accepting the sensor cable. In such embodiments, the gauge is conveniently and advantageously nonremovably associated with a particular sensor to avoid misplacement or misassociation.

In an embodiment, the digit gauge may be tab-shaped and comprise a semi-hardened plastic material. The digit gauge may include rounded edges to avoid discomfort during measuring.

An artisan will recognize from the disclosure herein a wide variety of possible gauge configurations capable of quickly and efficiently matching finger size to sensor. For example, the gauge may include multiple different sized openings, where each opening designates via color, text, or the like the appropriate sensor for that particular opening. The gauge may advantageously comprise a ring structure, a sleeve, or the like and shaped to fit a toe, thumb, fingers, or the like. Moreover, the gauge may function differently from the foregoing disclosure. For example, the opening may be sized such that when the finger fits through the opening, a smaller sensor should be used, when the finger does not fit, the sensor is appropriately matched, a larger sensor should be used, or the like.

Additionally, more complex gauges may be used that indicate electronically whether the finger is sized appropriately for the sensor. For example, the sensor may include LEDs that indicate an appropriate size, the instrument may supply feedback messages related to size, or the like. Such message or LED indications may be simply red for mismatched, yellow for borderline, and green for matched cross sectional finger size and sensor.

Although the finger gauge is disclosed with reference to its preferred embodiment, the disclosure is not intended to be limited thereby. Rather, a skilled artisan will recognize from the disclosure herein a wide number of alternatives accomplishing the same or similar functions. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

What is claimed is:

1. A noninvasive oximetry sensor, comprising:
a light source configured to emit light;
a detector configured to output a signal indicative of light attenuated by a digit of a patient; and
a finger gauge configured to determine proper sizing for said sensor, the gauge including:
a tab including an opening sized to determine whether a cross-section of said patient's digit is appropriate for said noninvasive sensor, wherein when a periphery of said cross-section is larger than an inner edge of said opening, said tab indicates that said digit is too large for said noninvasive sensor, said sensor configured to output a signal indicative of light attenuated by said digit, and
an association portion mechanically associating the tab with the sensor.

2. The noninvasive oximetry sensor of claim 1, wherein said association portion nonremovably associates the tab with the sensor.

3. The noninvasive oximetry sensor of claim 1, wherein said tab comprises plastic materials.

4. The noninvasive oximetry sensor of claim 1, wherein said tab comprises rounded edges about a periphery of said opening.

5. The noninvasive oximetry sensor of claim 1, wherein said tab further comprises indicia associated with said opening to identify its size.

6. The noninvasive oximetry sensor of claim 5, wherein said indicia comprises a color.

7. A method of determining whether a noninvasive optical sensor is sized to match a plurality of patients' body tissue, the sensor being configured to output a signal indicative of light attenuated by body tissues of said monitored patient, the method comprising:
sliding a finger gauge onto a first patient's finger, said finger gauge being mechanically associated with a cable of said sensor without being a portion of a housing of said sensor;
determining whether to use said sensor on said first patient's finger depending upon the fit of the gauge to said first patient's finger, wherein a poor fit indicates said sensor should not be used;
sliding said finger gauge onto a second patient's finger; and
determining whether to use said sensor on said second patient's finger depending upon the fit of the gauge to said second patient's finger, wherein a poor fit indicates said sensor should not be used.

8. The method of claim 7, wherein said sliding said mechanically associated finger gauge onto said finger comprises sliding a nonremovably associated finger gauge onto said finger.

9. The method of claim 7, wherein said sliding said finger gauge onto said finger comprises sliding said finger through one or more openings in said finger gauge, said openings bounded by rounded edges about their periphery.

10. The method of claim 9, comprising designating each of said one or more openings with indicia identifying a size of said opening.

11. The method of claim 10, wherein said designating comprises designating with indicia comprising differing colors.

12. A method of providing a noninvasive optical sensor with a finger sizing mechanism, the method comprising:
acquiring said optical sensor, said sensor including a light source and a detector configured to output a signal indicative of an attenuation of light by a finger of a monitored patient; and
mechanically associating a finger gauge with said optical sensor, said finger gauge having a fixed diameter and configured to determine whether said sensor is an appropriate size for said finger, wherein said sensor is configured to accommodate those finger sizes that meet said finger gauge.

13. The method of claim 12, wherein said mechanical associating comprising nonremovably associating said gauge with said sensor.

14. The method of claim 12, comprising sliding said finger into one or more openings in said finger gauge.

15. The method of claim 14, wherein said finger gauge includes rounded edges about the periphery of said one or more openings.

16. The method of claim 15, comprising designating each of said one or more openings with indicia identifying a size of said opening.

17. The method of claim 16, wherein said designating comprises designating with indicia comprising differing colors.

\* \* \* \* \*